US011674916B2

(12) United States Patent
Udrea et al.

(10) Patent No.: US 11,674,916 B2
(45) Date of Patent: Jun. 13, 2023

(54) GAS SENSOR

(71) Applicant: Sciosense B.V., Eindhoven (NL)

(72) Inventors: Florin Udrea, Cambridge (GB); Syed Zeeshan Ali, Cambridge (GB)

(73) Assignee: Sciosense B.V., AE Eindhoven (NL)

( * ) Notice: Subject to any disclaimer, the term of this patent is extended or adjusted under 35 U.S.C. 154(b) by 569 days.

(21) Appl. No.: 16/186,843

(22) Filed: Nov. 12, 2018

(65) Prior Publication Data
US 2020/0150066 A1 May 14, 2020

(51) Int. Cl.
*G01N 27/04* (2006.01)
*G01N 27/12* (2006.01)
*G01N 27/14* (2006.01)
*G01N 27/22* (2006.01)
*G01N 33/00* (2006.01)

(52) U.S. Cl.
CPC ......... *G01N 27/048* (2013.01); *G01N 27/128* (2013.01); *G01N 27/14* (2013.01); *G01N 27/225* (2013.01); *G01N 33/0036* (2013.01)

(58) Field of Classification Search
CPC .... G01N 27/048; G01N 27/128; G01N 27/14; G01N 27/225; G01N 33/0036
See application file for complete search history.

(56) References Cited

U.S. PATENT DOCUMENTS

| 9,506,885 | B2 | 11/2016 | Mayer |
| 9,746,437 | B1 | 8/2017 | Chiou et al. |
| 2003/0039586 | A1 | 2/2003 | Toyoda et al. |
| 2005/0199041 | A1 | 9/2005 | Weber et al. |
| 2006/0154401 | A1 | 7/2006 | Gardner et al. |
| 2007/0062812 | A1 | 3/2007 | Weber et al. |
| 2018/0292338 | A1 | 10/2018 | Liu et al. |

FOREIGN PATENT DOCUMENTS

| DE | 102015203050 A1 | 8/2016 |
| EP | 1936364 A1 | 6/2008 |
| EP | 2762865 A1 | 8/2014 |
| GB | 2533294 A | 6/2016 |

OTHER PUBLICATIONS

Yan, Guizhen, et al. "An experimental study on high-temperature metallization for micro-hotplate-based integrated gas sensors." Sensors and Actuators B: Chemical 86.1 (2002): 1-11. (Year: 2002).*

(Continued)

*Primary Examiner* — Robert J Eom
(74) *Attorney, Agent, or Firm* — Slater Matsil, LLP

(57) ABSTRACT

A gas sensing device comprising a substrate comprising an etched cavity portion and a substrate portion, a dielectric layer disposed on the substrate, wherein the dielectric layer comprises a dielectric membrane, wherein the dielectric membrane is adjacent to the etched cavity portion of the substrate, a heater located within the dielectric layer; a material for sensing a gas; and one or more polysilicon electrodes coupled with the material for sensing a gas.

11 Claims, 9 Drawing Sheets

(56) References Cited

OTHER PUBLICATIONS

Vergara, Alexander, et al. "An alternative global feature extraction of temperature modulated micro-hotplate gas sensors array using an energy vector approach." Sensors and Actuators B: Chemical 124.2 (2007): 352-359. (Year: 2007).*

Khanna, V. K., et al. "Design and electro-thermal simulation of a polysilicon microheater on a suspended membrane for use in gas sensing." (2007). (Year: 2007).*

Prasad, Mahanth, V. K. Khanna, and Ram Gopal. "Design and Development of Polysilicon-based Microhotplate for Gas sensing application." Sensors & Transducers 103.4 (2009): 44. (Year: 2009).*

De La Rica, Roberto, Cesar Fernandez-Sanchez, and Antonio Baldi. "Polysilicon interdigitated electrodes as impedimetric sensors." Electrochemistry Communications 8.8 (2006): 1239-1244. (Year: 2006).*

Briand, D., et al. "Highly Integrated Wafter Levels Packaged Mox Gas Sensors", Institute of Microtechnology, University of Neuchatel, Neuchatel, Switzerland, IEEE (2007); vol. 4A1.4, pp. 2401-2404, copyright 2007.

Briand, D., et al. "Design and fabrication of high-temperature micro-hotplates for drop-coated gas sensors" Elsevier Science; Sensors and Actuators B 68 (2000), pp. 223-233, copyright 2000.

International Search Report and Written Opinion from corresponding International Application No. PCT/EP2019/080231 dated Jan. 23, 2020, 15 pages.

International Search Report and Written Opinion from corresponding International Application No. PCT/EP2019/080372 dated Feb. 5, 2020, 16 pages.

\* cited by examiner

STATE OF THE ART

GAS SENSOR

TECHNICAL FIELD OF THE DISCLOSURE

The disclosure relates to gas sensors, particularly but not exclusively, to micro-machined metal oxide gas sensors.

BACKGROUND OF THE DISCLOSURE

Metal oxide (MOX) gas sensors are generally based on the deposition of a metal oxide film onto sensing electrodes defined on or within a suitable substrate. Micro-machined MOX gas sensors typically include a membrane, a heater element within the membrane, and electrodes in direct contact to the metal oxide (MOX) layer. A possible architecture of a MOX gas sensor is shown in FIG. 1 where the MOX layer is deposited on the membrane, opposite to the cavity formed by Deep Reactive Ion Etching (DRIE), or wet etching (see for example: D. Briand et al., "Design and fabrication of high temperature micro-hotplates for drop-coated gas sensors", Sensors and Actuators B, 68, pp. 223-233, 2000). The particular example depicted in FIG. 1 shows slanted walls, which can be achieved by wet etching. Vertical walls can be achieved by DRIE. The heater heats the sensitive layer at a certain temperature necessary for a chemical or physical reaction to a gas. The sensitive layer (i.e. MOX layer) changes its resistance/conductance in the presence of the gas. The resistance is measured across the electrodes, which may be arranged in an interdigitated configuration. The membrane serves to thermally isolate the MOX layer and heater to significantly reduce the power consumption. The MOX layer can be deposited using a variety of techniques, such as drop-coating, ink-jet, chemical vapour deposition (CVD) or screen printing, the first two being the most common. The membrane can be formed by a dielectric such as silicon nitrides or oxides. The substrate is typically silicon, but other semiconductor materials are possible.

It has been demonstrated in state-of-the-art to use gold or platinum electrodes. This extra deposition of gold and platinum increases process complexity and adds cost to the production of a device. Furthermore, neither gold nor platinum are CMOS compatible (due to possible formations of deep traps in the bandgap of the semiconductors) and issues with process integration of such layers post CMOS are challenging from a cost and supply chain perspective.

SUMMARY OF THE DISCLOSURE

This disclosure generally relates to micro-hotplates incorporating a membrane, a heater element within the membrane and polysilicon (e.g. interdigitated) electrodes in direct contact to a metal oxide (MOX) layer.

According to one aspect of the present disclosure, there is provided a gas sensing device comprising; a substrate comprising an etched cavity portion and a substrate portion; a dielectric layer disposed on the substrate, wherein the dielectric layer comprises a dielectric membrane, wherein the dielectric membrane is adjacent to the etched cavity portion of the substrate, a heater located within the dielectric layer; a material for sensing a gas; and one or more polysilicon electrodes coupled with the material for sensing a gas.

The polysilicon electrodes may be configured to measure a resistance of the material for sensing a gas.

The polysilicon electrodes may be highly doped. In other words, the electrodes may comprise n-doped or p-doped polysilicon with a doping concentration equal to or greater than $10^{17}$ cm$^{-3}$. Preferably, the doping concentration may be within the range $5 \times 10^{16}$ cm$^{-3}$ to $5 \times 10^{21}$ cm$^{-3}$. This improves the Ohmic contact to the material for sensing a gas.

The polysilicon electrodes may comprise a plurality of interdigitated structures, or fingers.

A width of at least some of the interdigitated structures and/or the distance between adjacent interdigitated structures within the plurality of interdigitated structures may have sub-micrometre dimensions.

The polysilicon electrodes may be formed in a CMOS compatible process.

The term "CMOS compatible process" covers the processing steps used within a CMOS process as well as covers certain processing steps performed separately from the CMOS process, but utilising processing tools usable in the CMOS processing steps.

Complementary metal-oxide-semiconductor (CMOS) technology is used to fabricate integrated circuits. The CMOS term refers to the silicon technology for making integrated circuits. CMOS processes ensure very high accuracy of processing identical transistors (up to billions), high volume manufacturing, very low cost and high reproducibility at different levels (wafer level, wafer to wafer, and lot to lot). CMOS comes with high standards in quality and reliability. The size of the CMOS features are below 2 microns, and are as low as 10 nm.

Not all silicon technologies are CMOS technologies. Examples of non-CMOS technologies include: lab technologies (as opposed to foundry technologies), screen printing technologies, bio-technologies as for example those employed in making fluidic channels, MEMS technologies, very high voltage vertical power device technologies, technologies that use materials which are not CMOS compatible, such as gold, platinum or radioactive materials. For example using non CMOS steps such as electro-plating of electrodes or using post CMOS steps such as lift-off to define the electrodes has the disadvantage that the size and pitches of the electrode fingers are much larger in dimensions (e.g. above 2 microns).

At least one of the polysilicon electrodes may be in direct contact with the material for sensing a gas. The polysilicon layer can be formed within the CMOS sequence and not post CMOS or pre CMOS or using a non CMOS process. As a result much lower dimensions for the width and pitch of the electrodes, as well as much better reproducibility of such dimensions, can be achieved.

The device may comprise a flip-chip configuration. The device may be packaged in a flip-chip configuration. In prior-art devices, deposition of gold and platinum comes with significant yield reduction, as well as the increased process complexity. In a flip-chip configuration, the use of polysilicon as interdigitated electrodes results in major simplification of the manufacturing process, cost reduction, and higher yield.

The flip-chip configuration also allows wafer level placement of a permeable membrane on top of the silicon substrate to protect the metal oxide gas sensing layer. This also reduces the effect of humidity and poisoning. The flip-chip configuration also enables connections of an electronic circuit (ASIC) via solder balls, solder bumps, or copper pillars. Advantageously, this reduces the form factor and eliminates the bond wires. This configuration may also allow for wafer level or chip level packaging.

An ASIC containing drive, read out, transducing, and processing circuitry may be attached to the sensor either by solder balls (or bumps) in the flip-chip configuration or by using Through Silicon Vias in the standard configuration. The ASIC may contain temperature and/or humidity sensors.

The heater may comprise a CMOS material. Optionally, the CMOS material may be any of polysilicon, platinum, titanium, tungsten, or a combination of these.

The heater may be formed underneath (or below) the polysilicon electrodes.

The dielectric membrane may comprise an etched recess portion, and the material for sensing a gas may be located within the etched recess portion of the dielectric membrane. The recess may be formed within the membrane, below one of the surfaces of the membrane and the gas sensing (or MOX) layer may be confined within the recess, making electrical and physical contact to the interdigitated polysilicon electrodes. The MOX may be deposited within the etched recess portion of the membrane and placed above/below the heater, but without making physical connection to the heater. To control the depth of the recess, an etch stop layer, such as a silicon nitride layer may be used. This silicon nitride layer may also separate the heater from the metal oxide (MOX) and may additionally act as a stress relief layer within the membrane.

The MOX layer may be fully embedded in the membrane so that the MOX layer is fully confined within the etched recess and cavity. The MOX layer surface is therefore below or largely below the surface of the membrane. This allows better confinement, which could improve both the reproducibility and reliability of the device. Confining the MOX layer reduces the spreading of the MOX layer on the surface of the membrane. In state-of-the-art devices this spreading causes reliability and reproducibility issues and also increases heat loss and, thus, power consumption.

Advantageously, this disclosure offers smaller dimensions of the MOX layer and thus smaller dimensions of the micro-hotplate. The confinement of the MOX layer in a cavity further results in
  i) better reproducibility;
  ii) reliability (as the MOX layer will be exposed to less temperature gradients); and
  iii) lower power consumption.

The gas sensing device may further comprise a plurality of first etch stop layers located on a top surface of the dielectric membrane, each first etch stop layer being located above a plurality of electrodes. Such etch stop layers could define the recess laterally and could locate and confine the MOX layer above the heater. The etch stop layers may have a higher resistance to the etchant used compared to the rest of the dielectrics in the membrane layers.

Each first etch stop layer may be laterally spaced from one another, or could form a ring or a closed shape at the surface. This helps define the recess laterally within the dielectric membrane, to avoid the MOX layer spreading towards the edge of the membrane. The etch stop layers may also help define the cavity within the substrate.

The etched recess portion may be defined or confined laterally by the plurality of first etch stop layers.

The gas sensing device may further comprise at least one second etch stop layer located within the dielectric layer, each second etch stop layer being located under a plurality of electrodes. The second etch stop layer may define vertically the depth of the gas sensing material and may preferably isolate the MOX layer from the heater.

The at least one second etch stop layer below the electrodes may extend laterally through the entire dielectric membrane area. The etch stop layer may provide stress relief, and therefore an etch stop layer extending laterally through the entire membrane can strengthen the membrane.

The second etch stop layer may extend through an entire width of the dielectric layer, providing stress relief and strengthening through the dielectric layer.

The material used for such etch stop layer could be for example silicon nitride. A preferred way to form this etch stop layer is LPCVD (Low Pressure Chemical Vapour Deposition).

The etched recess portion of the dielectric membrane may be formed on a front side of the dielectric layer. This allows an etched recess in a non flip-chip configuration. The etched recess portion of the dielectric membrane may be formed over the etched cavity portion of the substrate.

The etched recess portion of the dielectric membrane may be formed on a back side of the dielectric layer. This allows an etched recess in a flip-chip configuration. The etched recess portion of the dielectric membrane may be formed within the etched cavity portion of the substrate.

The etched recess portion may be formed by wet etching of part of the dielectric membrane using at least one etch stop layer to prevent further lateral or vertical etching.

Alternatively, the etched recess portion may be formed by dry or a combination of dry and wet etching of part of the dielectric membrane using at least one etch stop layer to prevent farther lateral or vertical etching.

The etched recess portion may be formed at the same time (in the same step) as the membrane, during the cavity etching by using an addition wet etching of the dielectric membrane. The wet etching would not use any of the etch stop layers or the electrodes. This method to form the recess portion has the advantage that the etched cavity (to define the membrane) and the etched recess portion (where the gas sensing layer is to be confined) are formed within the same step.

The etched recess portion may extend underneath the polysilicon electrodes. This allows more contact between the gas sensing material and the electrodes, and can improve sensitivity of the device.

The etched recess portion may not directly contact the heater to avoid the electrical connection of the material for sensing a gas with the heater.

The material for sensing a gas may extend underneath the polysilicon electrodes. In other words, a substantial part of the gas sensing material (MOX) is placed below the electrodes. This allows the electrodes to be closer to the surface of the gas sensing material. This increases sensitivity of the device. The feature of embedding the gas sensing material, partly or entirely, in the membrane has the advantage of the electrodes closer to the surface of the gas sensing material and greater control of the size, the form, and placement within the membrane of the gas sensing material.

The material for sensing a gas may not extend above an upper surface of the dielectric membrane. Alternatively, the material for sensing a gas may be completely confined below an upper surface of the dielectric membrane.

The material for sensing a gas may be embedded in the dielectric membrane. In other words, the material for sensing a gas may not extend beyond a surface of the dielectric membrane and may be entirely embedded in the dielectric membrane.

The material for sensing a gas may not be formed underneath the polysilicon electrodes. In other words, the material for sensing a gas may not be formed directly underneath or below the electrodes, and may only be formed above the electrodes and extending downwards in the gap between the electrodes. This can make the fabrication process simpler and provide mechanical support to the electrodes.

The polysilicon electrodes may comprise a first polysilicon layer, and the heater may comprise a second polysilicon layer.

The polysilicon electrodes may comprise a first polysilicon layer and a second polysilicon layer.

The polysilicon electrodes may comprise a first pair of electrodes comprising interdigitated electrodes, and a second pair of electrodes interleaving between the first pair of electrodes. The first pair of electrodes may be configured such that a current bias is applied across them, and the second pair of electrodes may be configured to measure a voltage between them.

Preferably, this 4-way electrode configuration may comprise two sets of interdigitated electrodes, and two electrodes interleaving between the fingers of the two interdigitated electrodes. A current bias may be applied across the two interdigitated electrodes, and the voltage may be measured across the two interleaving electrodes. Using polysilicon in this arrangement is preferable as polysilicon patterning techniques allow good resolution of the fingers and can pack the electrodes in a small space.

Alternatively, other electrode configurations may also be used, including having four rectangular parallel electrodes, where current bias is applied to the outer most electrodes, while the voltage is measured on the inner two electrodes. Several other electrode designs are also possible.

CMOS technologies offer the polysilicon width (which normally defines the length of the MOS gate of CMOS transistors) as the smallest dimension controllable in the manufacturing process. Therefore polysilicon electrodes with widths of sub-micrometre dimensions can be manufactured. The distance between adjacent fingers of the electrodes may also be of sub-micrometres. This aspect ratio results in a much denser structure of electrodes, which further lowers the resistance of the gas sensing layer. This is particularly useful in situations where the resistances of the MOX layers are very high (MΩ range) and the high aspect ratio allows them to be reduced to below 1 MΩ.

The first pair of electrodes may comprise two connections for the current to flow through the MOX gas sensing layer and two further connections for resistance or voltage measurement of the gas sensing layer. This allows the removal of the undesirable effects of the contact resistance. This contact resistance can introduce yield losses and non-uniformity from device to device or batch to batch. The contact layer can also drift in time. Furthermore, its resistance is not affected by the chemical reaction and therefore the sensitivity and selectivity to a particular gas may be lowered or worsened.

Advantageously, this 4-way measurement results in removing the contact resistance and thus increasing the sensitivity, the selectivity and enhancing the reliability as the contact resistance can deteriorate in time. It also lowers the sensing resistances making the measurement circuit less complex.

A width of at least some of the polysilicon electrodes may be of sub-micrometre dimension. The length of the polysilicon electrodes may be substantially larger than the width of the polysilicon electrodes, such that the polysilicon electrodes have a high aspect ratio.

According to a further embodiment of the disclosure, there is provided a gas sensor array assembly comprising an array of a plurality of gas sensing devices as described above, wherein the plurality of gas sensing devices may be formed on the same chip. The sensing devices may have the same gas sensing materials or different gas sensing materials, and may be operated at different temperatures of driving conditions.

This allows a gas sensor array assembly which is selectively sensitive to different gases or provides a dual or differential output.

According to a further aspect of the disclosure, there is provided a method of manufacturing a gas sensing device, the method comprising: forming a substrate; forming a dielectric layer disposed on the substrate; forming a heater within the dielectric layer; forming an etched cavity portion within the substrate; forming a material for sensing a gas; and forming one or more polysilicon electrodes coupled with the material for sensing a gas.

Forming one or more polysilicon electrodes may comprise: forming a field stop oxide (or gate oxide) layer in a CMOS compatible process; forming one or more polysilicon electrodes on or above the field stop oxide layer; and etching the field stop oxide layer.

Forming one or more polysilicon electrodes may comprise: forming a first polysilicon layer comprising a first pair of electrodes in a CMOS compatible process; and forming a second polysilicon layer comprising a second pair of electrodes in a CMOS compatible process.

Compared to the state-of-the-art gas sensors, the sensing device disclosed has polysilicon electrodes which offer CMOS compatibility, and may have the following features:

i) 4 way measurement of the MOX layer using an additional pair of electrodes which could be made of polysilicon or another material such as tungsten;
ii) a recess portion to confine the MOX layer;
iii) at least one etch stop layer to control the form and the position of the recess and preferably separate physically and electrically the MOX from the heater; and
iv) embedding partly or fully the MOX within the recess formed within the membrane.

Compared to state-of-the-art sensing devices, the gas sensing device disclosed may have the following advantages:

i) Use of polysilicon electrodes such that no post CMOS processing would be required except for the membrane etching and the packaging;
ii) Polysilicon electrodes can be manufactured on a sub-micrometre scale with a high aspect ratio, therefore increasing sensitivity of the device;
iii) Confinement of the MOX layer within a recess portion to reduce the spreading of the MOX layer on the surface of the membrane;
iv) Use of at least one etch stop layer to define the recess in a reproducible way and possibly to avoid the metal oxide (MOX) to be in physical or electrical contact with the heater layer. Such etch stop layer could be a silicon nitride layer, formed within a largely made silicon dioxide membrane. Such nitride layer could also be used as stress relief layer within the membrane;
v) Increased reliability and reproducibility, and reduced heat loss and power due to reduction of spreading of the MOX layer;
vi) Smaller form factor, as the confinement minimises the spot size of the MOX layer and thus the size of the membrane;
vii) Preferably reduced package cost, as the ASIC will be bonded via solder balls or TSVs and would not require bond wires. Possibly the packaging could also be done at wafer level.

BRIEF DESCRIPTION OF THE PREFERRED EMBODIMENTS

Some preferred embodiments of the disclosure will now be disclosed by way of example only and with reference to the accompanying drawings, in which:

FIGS. 13A-C illustrate exemplary manufacturing steps of a gas sensor according to one embodiment, wherein:

FIG. 13A shows the dielectric membrane with polysilicon electrodes, etch stop layers, and a heater embedded within the membrane;

FIG. 13B shows the device of FIG. 13A which has then been exposed from the back side to an etchant forming a recess within the dielectric membrane; and FIG. 13C shows the device of FIG. 13B which has then been flipped upside down with a sensing material confined within the etched recess.

DETAILED DESCRIPTION OF THE PREFERRED EMBODIMENTS

Some examples of the device are given in the accompanying figures.

Figure 1:
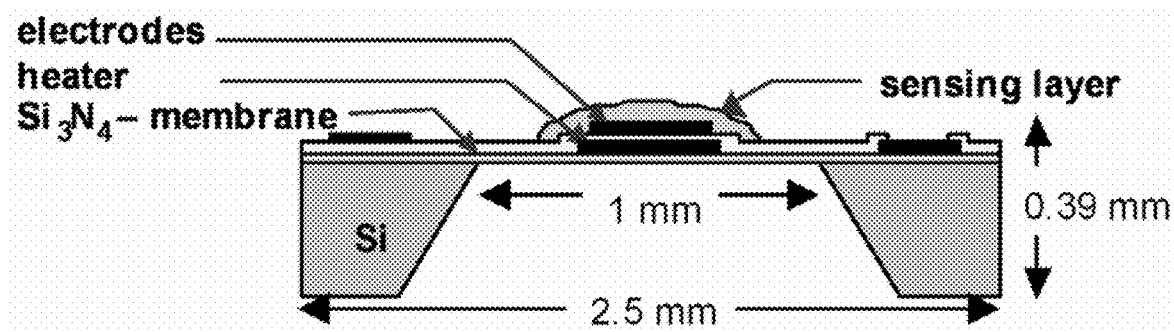
FIG. 1 illustrates a gas sensing device according to the state of the art.
Figure 2:
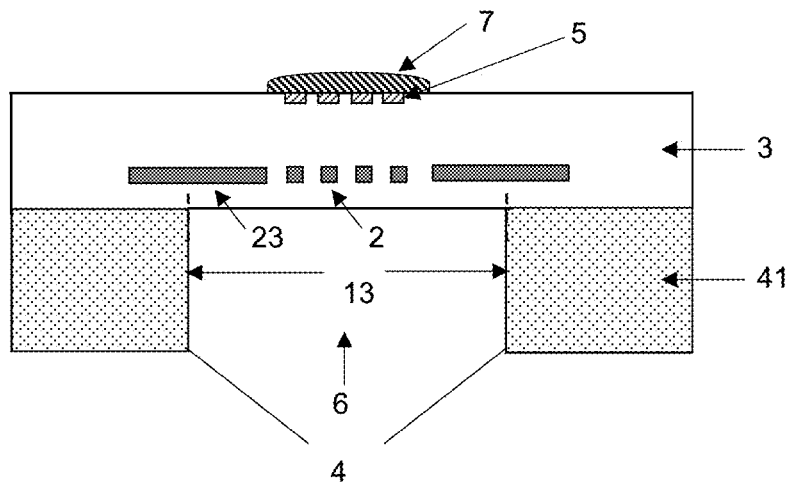
FIG. 2 shows a schematic cross-section of a gas sensor based on a micro-hotplate according to one embodiment.

FIG. 2 shows a cross section of an exemplary gas sensor 1. The gas sensor 1 comprises a dielectric layer 3 supported by a semiconductor substrate 41 which has an etched portion 6 and a substrate portion 4. In one example, the semiconductor substrate 41 can be made of silicon or silicon carbide. The dielectric layer 3 has a dielectric membrane region or area 13, which is located immediately or directly adjacent or next to the etched portion or cavity 6 of the substrate 41. In one example, the dielectric layer 3 can be made from a material such as silicon oxide, nitride, or a combination of these. The dielectric membrane area 13 corresponds to the area of the dielectric layer 3 (directly) above or below the etched portion 6. The substrate 41 is etched by DRIE to form the etched portion or cavity 6.

A gas sensing material 7 is deposited or grown on the dielectric membrane 13. The gas sensing material 7 makes electrical contact to a pair of interdigitated polysilicon electrodes 5 which are formed within the dielectric layer 3. The polysilicon electrodes are configured to measure resistance and/or capacitance of the gas sensing material 7. A heater 2 and heater tracks 23 are embedded within the dielectric layer 3, which when powered raises the temperature of the gas sensing MOX layer 7. The heater 2 is formed within the dielectric membrane area 13. In this embodiment, the heater 2 is a micro-heater and can be made from a metal such as Tungsten, Platinum, Gold, or Titanium.

In one example, the gas sensing material 7 can be a metal oxide such as tin oxide, tungsten oxide, Alumina oxide, zinc oxide, copper oxide, a combination of those metal oxides, or other metal oxides. In further examples, the gas sensing material 7 can be un-doped or doped with elements such as platinum (Pt) or palladium (Pd). Alternatively, the gas sensing material could be a polymer or a nanomaterial such as carbon nanotubes or metal oxide nanowires.

The use of polysilicon for the electrodes allows the whole gas sensing device to be manufactured using CMOS compatible processes. Polysilicon electrodes can be manufactured to sub-micrometre dimensions, allowing greater length of electrode to be packed into a smaller area, with higher aspect ratio. The plurality of polysilicon electrodes may be formed of a first polysilicon layer, and the heater may be formed of a second polysilicon layer.

Figure 3:
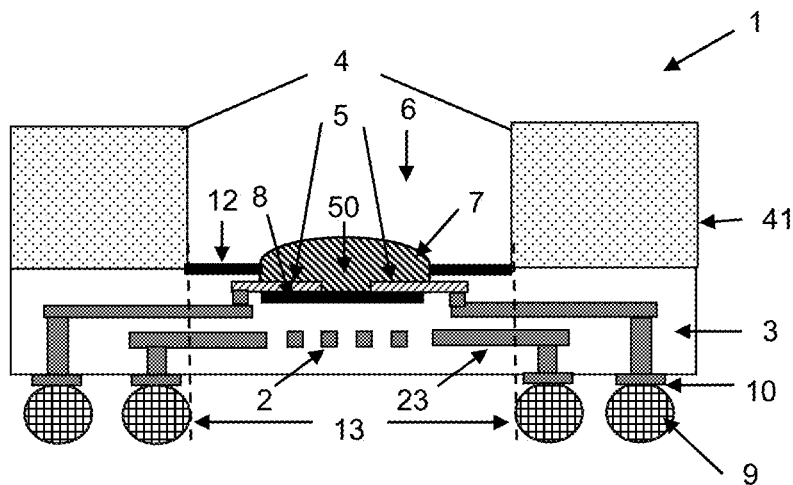
FIG. 3 shows a schematic cross-section of an upside-down gas sensor wherein a recess is formed within the dielectric membrane according to one embodiment.

FIG. 3 shows an alternative gas sensor in which the sensor has an upside-down configuration. The dielectric membrane region 13 is patterned or etched such there is a recess 50 in the dielectric membrane region 13 for the gas sensing MOX material 7 to be positioned or confined, when deposited from one side (e.g., from the back side) of the dielectric membrane region 13. An etch stop layer 8 is formed within the dielectric membrane region 13, below the polysilicon electrodes 5. A further etch stop layer 12 is formed on the top of the dielectric membrane region 13, except at the region where the gas sensing material 7 is to be formed. The etch stop layers 8, 12 may be silicon nitride or any other material having a higher resistance to the etchant used to etch the semiconductor substrate 4 and/or the dielectric membrane 13. The silicon nitride layers 8, 12 act as an etch stop, allowing a recess 50 to be etched in the membrane 13. The silicon nitride layers 8, 12 also provide stress relief and define the cavity 6. The gas sensing material 7 is formed within the etched recess 50, on the dielectric membrane region 13. It will be understood that the etch stop layers 8, 12 may be formed of silicon nitride or may be formed of other materials which have different etch selectivity to the rest of the membrane.

A gas sensing material 7 is deposited or grown within the substrate cavity 6, in the recess 50 of the dielectric membrane 13. The polysilicon electrodes 5 are in direct contact with the gas sensing material 7. The heater is formed below or underneath the polysilicon electrodes. In the manufacturing process, a high temperature is used for deposition of the polysilicon electrodes. This upside-down sensor configuration allows the polysilicon electrodes to be formed using high temperature without damaging the metal heater underneath. This is because in the upside down configuration, the polysilicon sensing electrodes are deposited before the metal heater, and so the high deposition temperature of the polysilicon cannot damage the heater. Since the device is then turned upside down after fabrication, the polysilicon electrodes are then above the heater.

The gas sensor 1 is formed in a flip-chip configuration. The gas sensor can be placed above a circuit (e.g. an application specific integrated circuit (ASIC) or printed circuit board (PCB)), using Solder balls, solder bumps, copper pillars, or stud bumps 9 for connection. The solder balls 9 are typically placed on solderable pads, 10, and can be formed within the CMOS process or post-CMOS at wafer level or chip level on both the IR device and the ASIC.

Figure 4:
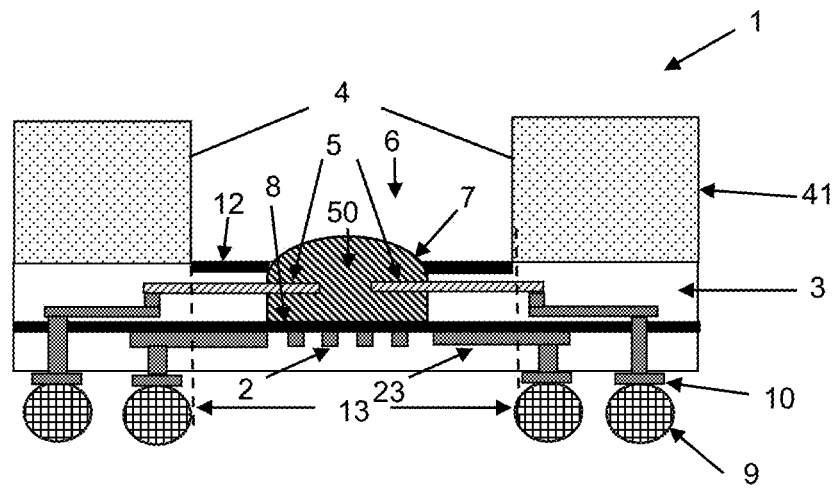
FIG. 4 shows a schematic cross-section of an upside-down gas sensor, where the polysilicon electrodes are within the sensing layer instead of at the bottom of the sensing layer according to one embodiment.
Figure 5:
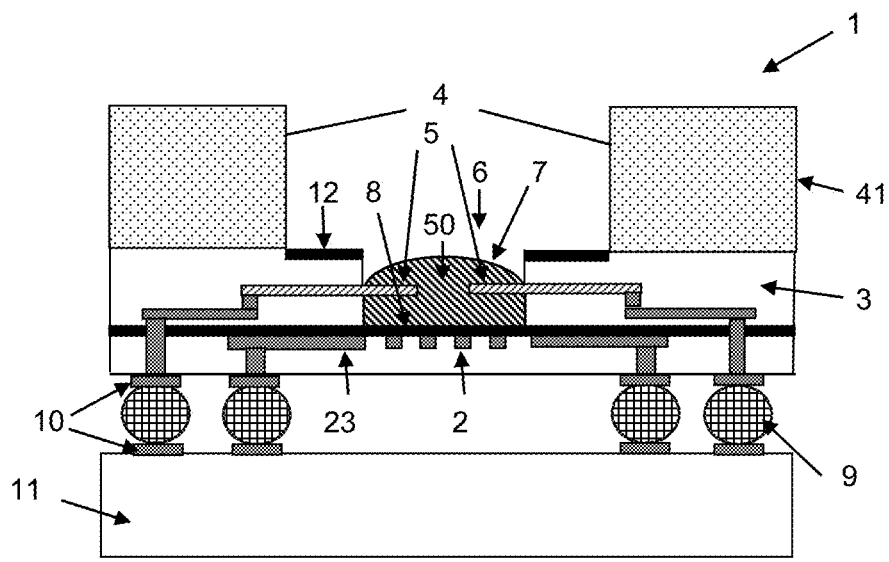
FIG. 5 shows a schematic cross-section of an upside-down gas sensor flip-chip connected to another chip such as an ASIC according to one embodiment.

FIG. 4 shows an alternative gas sensor in which the polysilicon electrodes 5 are located vertically within the MOX sensing layer 7. In other words, the polysilicon electrodes 5 extend laterally from a middle portion of each side wall of the MOX sensing layer 7. Many features of the gas sensor of FIG. 4 are the same as those in FIG. 3, and therefore carry the same reference numerals. In this embodiment, the silicon nitride layer 8 is formed deeper in the dielectric layer 3 than the polysilicon electrodes 5. This allows the etching to continue further into the dielectric membrane area 13, and means that part of the MOX gas sensing material 7 is below the polysilicon electrodes 5. This allows more contact between the gas sensing material 7 and the sensing electrodes 5. In this embodiment, the silicon nitride layer 12 extends across the whole width of the dielectric 3 or the gas sensor 1. The silicon nitride layers 8, 12 help to relieve stress within the device FIG. 5 shows an alternative gas sensor, in which the gas sensor is attached by a flip-chip to a second chip, such as an ASIC. Many features of the gas sensor of FIG. 5 are the same as those in FIG. 4 and therefore carry the same reference numerals. In this embodiment gas sensor 1 is attached to an ASIC chip 11 by solder balls 9 and solderable pads 10. This chip has driving, read out, transducing, and processing circuitry. It may include analogue, digital, or mixed signal analogue and digital circuits. It may also include humidity and/or temperature and/or pressure sensors. It may include memory blocks and state machines.

In this embodiment, a substantial part of the gas sensing MOX material, 7 is underneath or below the polysilicon electrodes 5, which means that the polysilicon electrodes 5 are closer to the surface of MOX material 7. Thin gas sensing MOX layers have increased sensitivity in comparison with thicker MOX layers. Using traditional inkjet or drop coating techniques on plain surfaces without a cavity, results in relatively thick and uncontrolled sizes of the MOX layer 7. In this gas sensor the effect of embedding, partly or entirely, the MOX within the membrane has the advantage of an equivalent thinner layer (with the polysilicon electrodes closer to the MOX surface that is exposed to the gas) and more controlled size of MOX layer.

Figure 6:
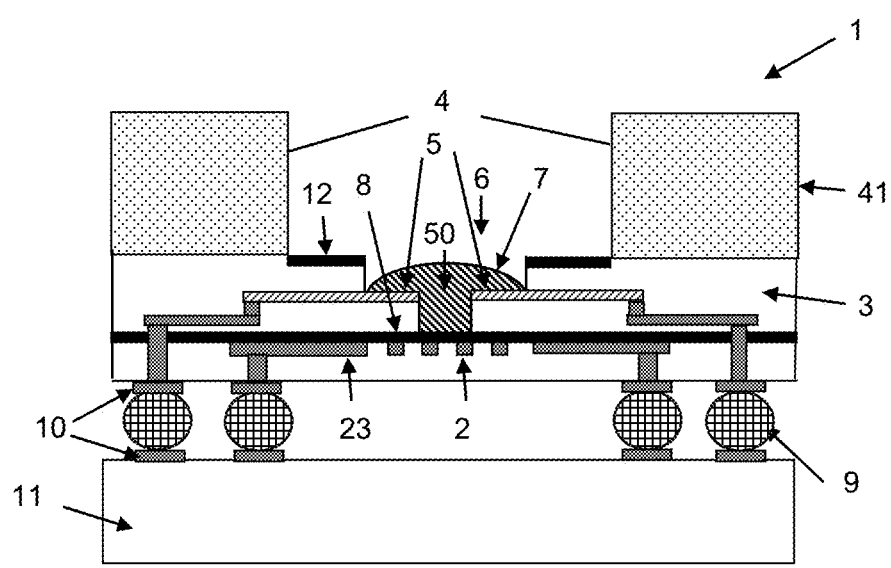
FIG. 6 shows an alternative structure for an upside-down gas sensor flip-chip connected to another chip in the form of an ASIC according to one embodiment.

FIG. 6 shows an alternative gas sensor, in which the gas sensing material is only formed in the spacing between the polysilicon electrodes, and not below the polysilicon electrodes. Many of the features of the gas sensor of FIG. 6 are the same as those shown in FIG. 5, and therefore carry the same reference numerals.

Figure 7:
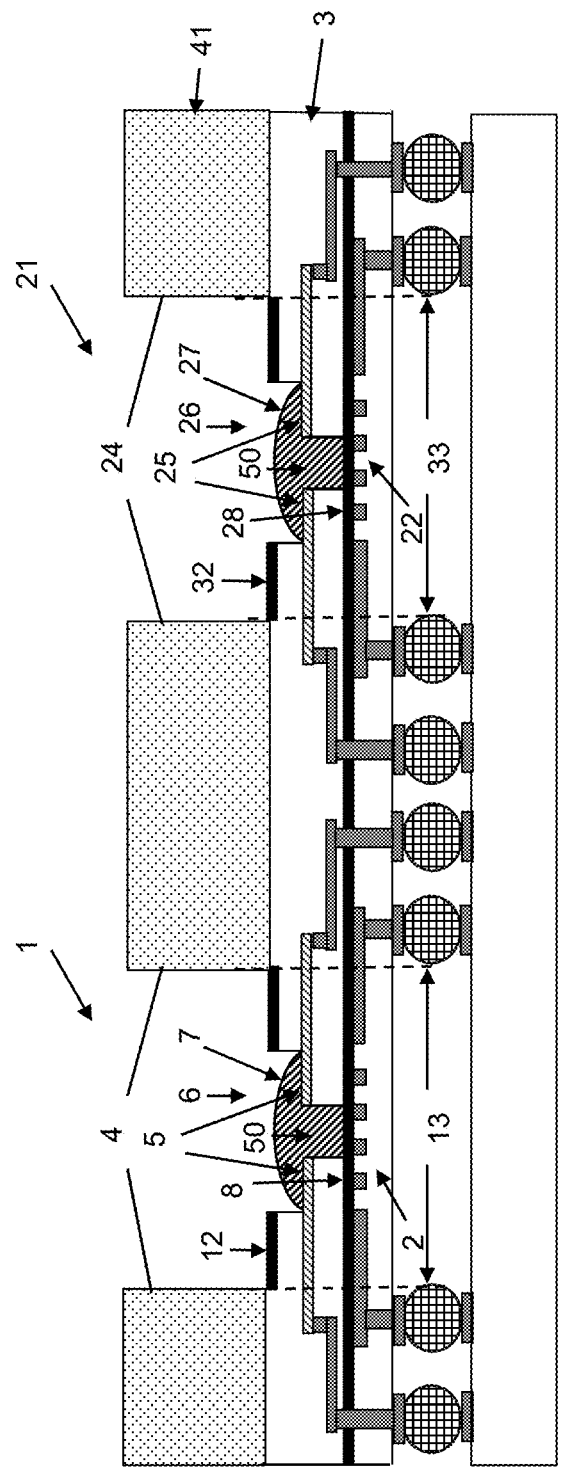
FIG. 7 shows a schematic cross-section of an array of upside-down gas sensors flip chip connected to another chip.

FIG. 7 shows an array of gas sensors in a flip-chip configuration, according to one embodiment. Many of the features of FIG. 7 are the same as those shown in FIG. 6, and therefore carry the same reference numerals. This can be any number of sensors 1, 21, each having either the same MOX gas sensing 7, 27 material, or a different MOX gas sensing material, and may be operated at different temperatures and different driving conditions. The gas sensors are formed within the same dielectric layer 3, on separate dielectric membranes 13, 33. The membranes 13, 33 can also be of different sizes within the array.

Figure 8:
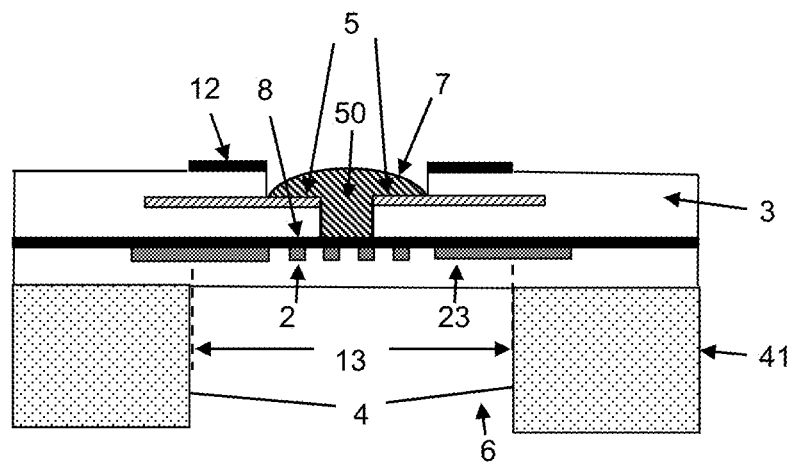
FIG. 8 shows a schematic cross-section of an alternative gas sensor where the membrane recess is present on the top side of the membrane rather than the bottom side according to one embodiment.

FIG. 8 shows an alternative gas sensor with a non flip-chip configuration. Many of the features of FIG. 8 are the same as those shown in FIG. 5, and therefore carry the same reference numerals. In this embodiment, the front side of the dielectric membrane region 13 is etched to form a recess 50 in the dielectric membrane. The gas sensing MOX material 7 is formed partly or fully embedded in the dielectric membrane. The gas sensor can be connected to an ASIC using wire bonding or Through Silicon Vias (not shown).

Figure 9:
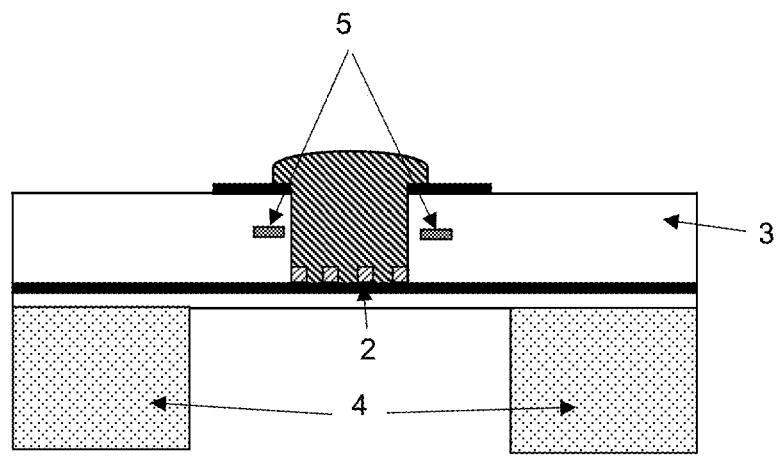
FIG. 9 shows a schematic cross-section of an alternative gas sensor with a ring metal heater.

FIG. 9 shows an alternative gas sensor in which the electrodes 5 have a ring formation. This embodiment is not formed in a flip-chip configuration, and so can be packaged in a conventional way. In this configuration the polysilicon is deposited before the metal heater. Therefore, the high temperatures required during polysilicon deposition don't affect the metal heater.

Figure 10:
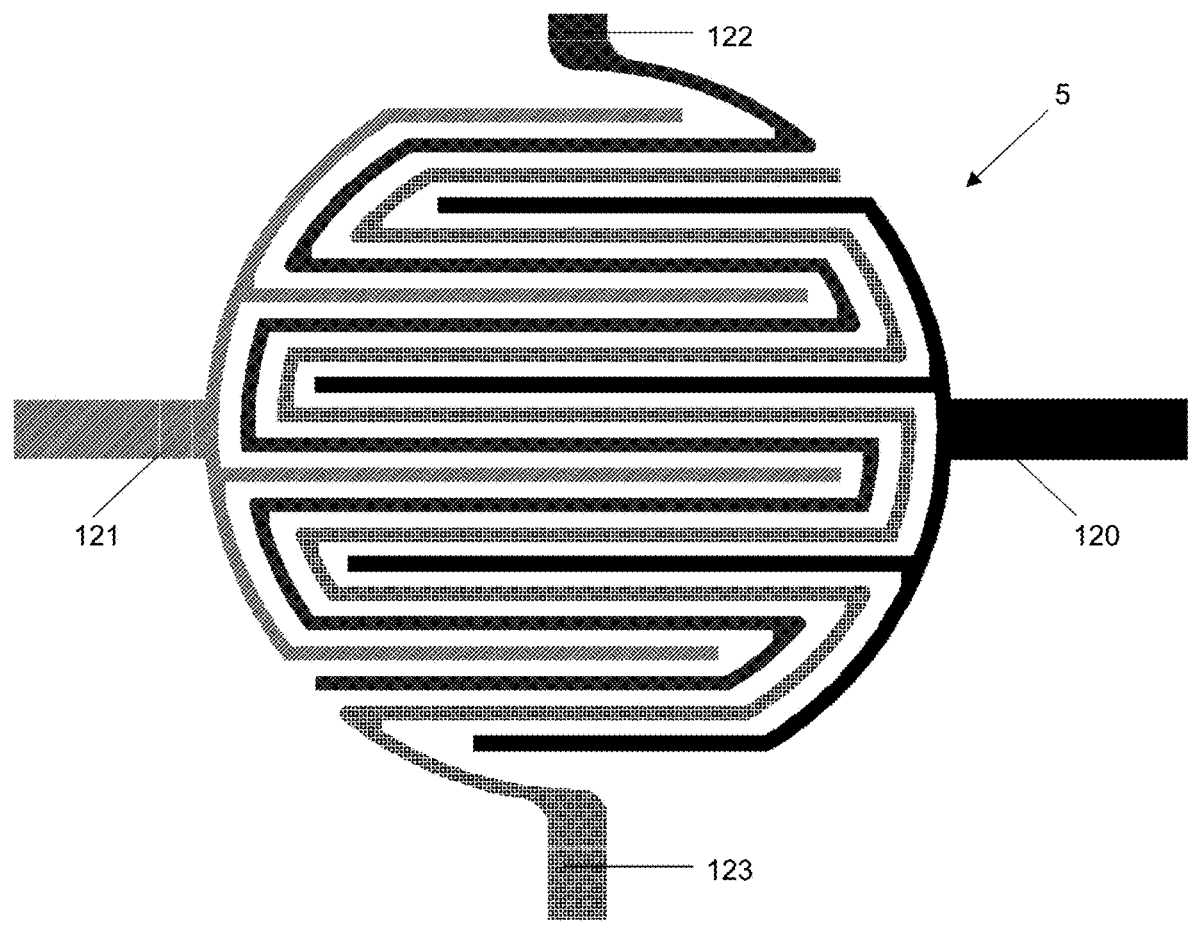
FIG. 10 shows a top view of polysilicon electrodes according to one embodiment.

FIG. 10 illustrates a top view of the polysilicon electrodes according to one embodiment. A first pair of interdigitated polysilicon electrodes 120, 121 is configured such that a current bias is applied across them, and a second pair of interleaving electrodes 122, 123 is configured to measure a voltage. The first pair of electrodes 120, 121 has an interdigitated (finger) structure. The second pair of electrodes 122, 123 interleave between fingers of the first pair of electrodes 120, 121. The width of each of the interdigitated or interleaved electrode structures and/or the distance between adjacent electrode structures has preferably sub-micrometre dimensions. Patterning techniques for polysilicon allow this resolution of the interdigitated electrode structure, meaning the electrodes can be packed or fitted into a small area.

CMOS technologies offer the polysilicon width (which normally defines the length of the MOS gate of CMOS transistors) as the smallest dimension controllable in the manufacturing process. Therefore polysilicon electrodes with widths of sub microns can be formed. The distance between adjacent fingers of the electrode pair could also be of sub-micrometres. This high aspect ratio results in a much denser structure of electrodes which further lowers the resistance of the gas sensing layer. This is particularly useful in situations where the resistances of the MOX layers are very high (M$\Omega$ range) and the high aspect ratio allows them to be reduced to below 1 M$\Omega$.

This 4-wire measurement configuration allows the resistance of the gas sensing material 7 to be measured while cancelling out effects of contact resistances. This results in improved sensitivity of the gas sensing device. This also lowers the sensing resistances, therefore making the measurement circuit less complex.

Figure 11:
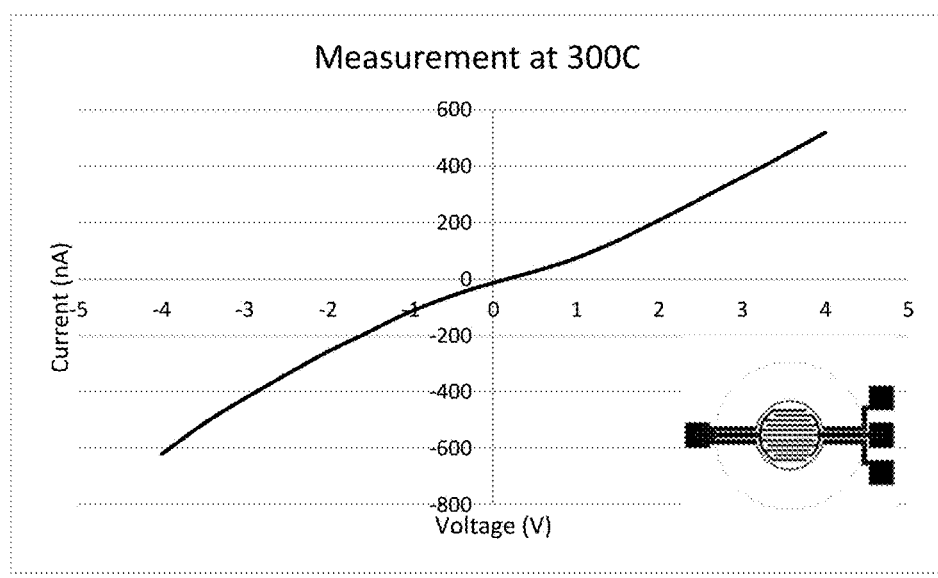
FIG. 11 shows measurements illustrating polysilicon electrodes forming an Ohmic contact to a metal oxide according to one embodiment.

FIG. 11 shows the measured current-voltage (I-V) characteristics of the metal oxide when a single pair of polysilicon interdigitated electrodes is used. The measurements show an Ohmic contact between the polysilicon and the MOX.

Figure 12:
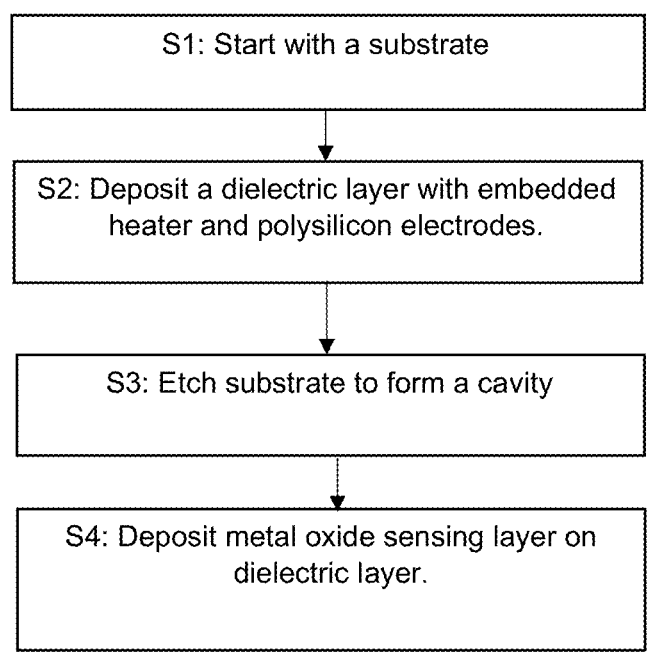
FIG. 12 illustrates an exemplary flow diagram outlining the manufacturing method of the gas sensor.

FIG. 12 illustrates an exemplary flow diagram outlining the manufacturing method of the gas sensor. The steps generally performed are described below. It will be appreciated that the steps below could be sequential or non-sequential:

Step 1 (S1): Start with a substrate.

Step 2 (S2): Deposit a dielectric layer with embedded heater and polysilicon electrodes. Etch stop layers may also be formed.

Step 3 (S3): Etch substrate to form a cavity.

Step 4 (S4): Deposit metal oxide sensing layer within the recess.

In embodiments where the membrane has an etched recess, the method may also include a step of etching the dielectric layer. This may be done using the etch stop layers, as the etchant will not etch the stop layers or the electrodes. This may be carried out in a single step with step 2, by using a deep reactive ion etch for the cavity etch followed by a wet oxide etch for the recess.

Figure 13A:
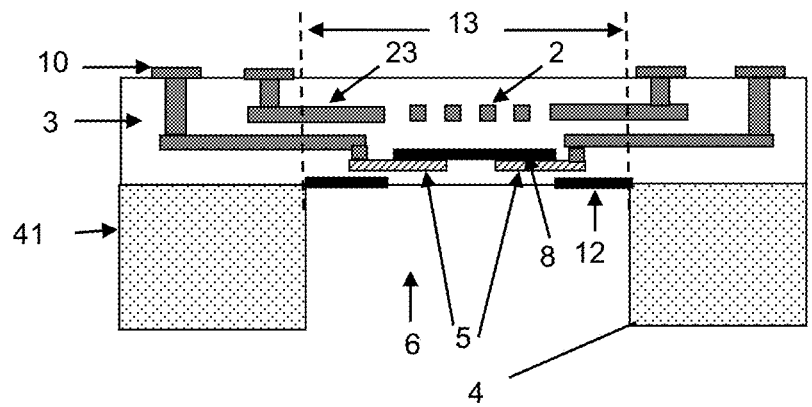
Figure 13B:
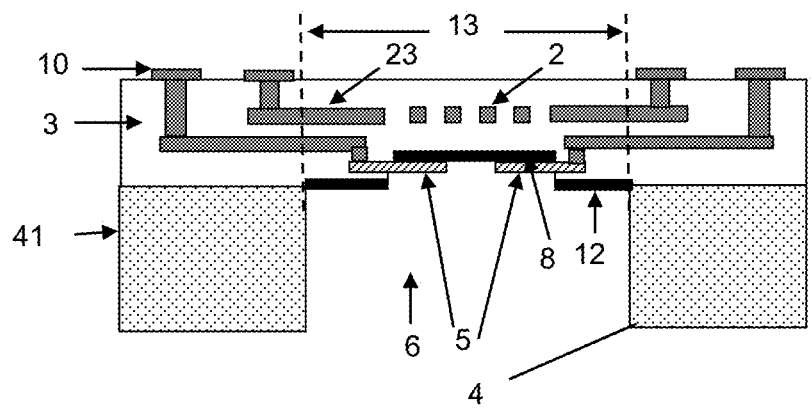
Figure 13C:
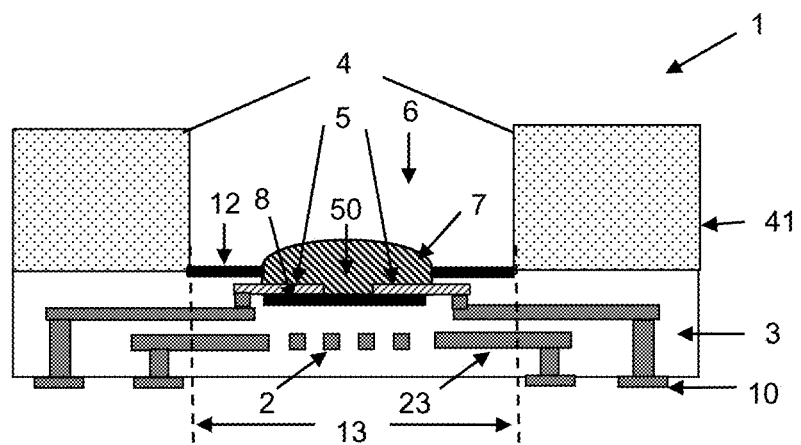

FIGS. 13A-C show some example steps of forming the recess and exposing the sensing electrodes, according to one embodiment of the disclosure.

FIG. 13A shows the dielectric membrane 13, with polysilicon electrodes 5 and heater 2 embedded within the membrane 13. Layers 8 and 12 are made from a material that has different etching properties to that of the dielectric layer 3.

FIG. 13B shows the device of FIG. 13A which has then been exposed from the back side to an etchant that has a high etching rate to the membrane, but a low etching rate to layers 8 and 12. This etches the dielectric layer below the etch stop layers 8, 12 forming a recess.

FIG. 13C shows the device of FIG. 13B which has then been flipped upside down. A sensing material 7 has been deposited so that it is confined within the recess.

Figure 14:
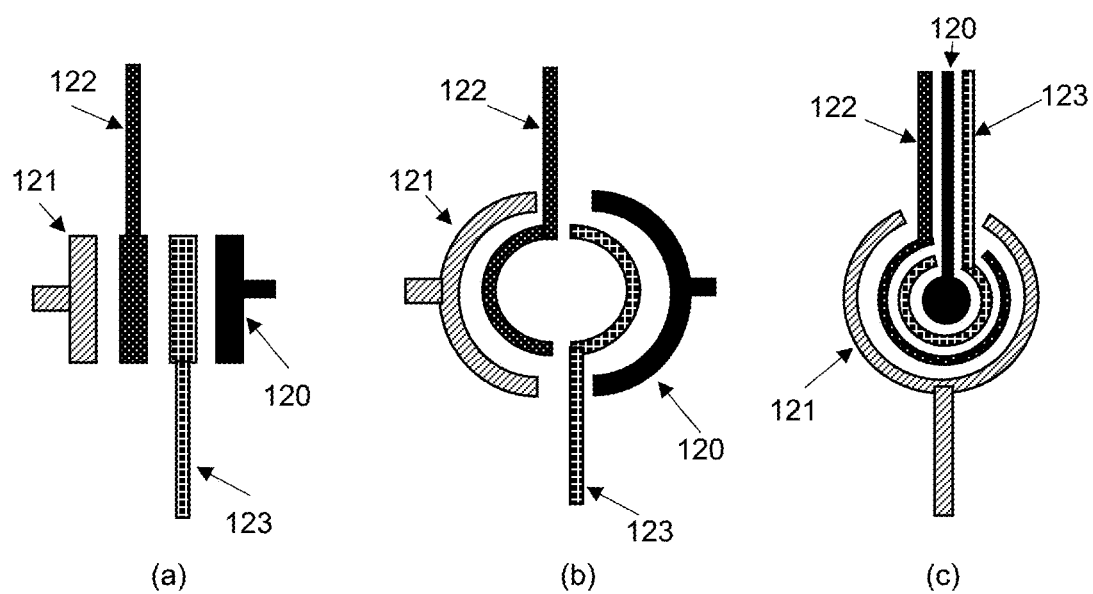
FIG. 14 illustrates further electrode arrangements that may be used.

FIG. 14, part (a) illustrates an electrode configuration with four rectangular parallel electrodes. In this arrangement current bias is applied to the two outer most electrodes, and voltage is measured on the two inner electrodes.

FIGS. 14, part (b) and 14, part (c) illustrates further arrangements of the electrodes that may be used.

The description of the reference numerals used in the above description is as follows:

1. Gas sensor
2. Embedded micro-heater embedded in the dielectric membrane
23. Heater tracks
3. Dielectric layer
13. Dielectric membrane area
4. Semiconductor substrate
41. Substrate portion
5. Polysilicon interdigitated electrodes
6. Cavity within the substrate
7. Metal oxide sensing layer
8. Silicon nitride layers (below polysilicon electrodes)
9. Solder balls, solder bumps, copper pillars or stud bumps
10. Solderable pads
11. ASIC.
12. Silicon nitride layers (on the surface of the dielectric membrane)
50. Recess within the dielectric membrane
21. Gas sensor
22. Embedded micro-heater embedded in the dielectric membrane
24. Semiconductor substrate
25. Polysilicon interdigitated electrodes
26. Cavity within the substrate
27. Metal oxide sensing layer
28. Silicon nitride layers (below polysilicon electrodes)
32. Silicon nitride layers (on the surface of the dielectric membrane)
120. Interdigitated polysilicon electrode 120
121. Interdigitated polysilicon electrode
122. Interleaving electrode
123. Interleaving electrode The skilled person will understand that in the preceding description and appended claims, positional terms such as 'above', 'overlap', 'under', 'lateral', 'vertical', etc. are made with reference to conceptual illustrations of a sensing device, such as those showing standard cross-sectional perspectives and those shown in the appended drawings. These terms are used for ease of reference but are not intended to be of limiting nature. These terms are therefore to be understood as referring to a sensing device when in an orientation as shown in the accompanying drawings.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A gas sensing device comprising:
   a substrate comprising an etched cavity portion and a substrate portion;
   a dielectric layer disposed on the substrate, wherein the dielectric layer comprises a dielectric membrane, and wherein the dielectric membrane is adjacent to the etched cavity portion of the substrate;
   a heater located within the dielectric layer;
   a material configured to sense a gas; and
   one or more polysilicon electrodes coupled and in direct contact with the material configured to sense the gas, wherein the one or more polysilicon electrodes comprise a first pair of electrodes comprising interdigitated electrodes and a second pair of electrodes interleaving between the first pair of electrodes, and
   wherein the polysilicon electrodes comprises two connections configured for current flow through the material configured to sense the gas and two further connections configured for resistance or voltage measurement of the material configured to sense the gas.

2. The gas sensing device according to claim 1, wherein the one or more polysilicon electrodes are highly doped.

3. The gas sensing device according to claim 1, wherein a width of at least some of a plurality of interdigitated structures and/or a distance between adjacent interdigitated structures within the plurality of interdigitated structures have sub-micrometer dimensions.

4. The gas sensing device according to claim 1, wherein the one or more polysilicon electrodes are formed in a CMOS compatible process.

5. The gas sensing device according to claim 1, wherein the gas sensing device comprises a flip-chip configuration.

6. The gas sensing device according to claim 1, wherein the heater comprises a CMOS material, and optionally wherein the CMOS material is any of polysilicon, platinum, titanium, tungsten, or a combination of these.

7. The gas sensing device according to claim 1, wherein the heater is formed underneath the one or more polysilicon electrodes.

8. The gas sensing device according to claim 1,
   wherein the dielectric membrane comprises an etched recess portion, and
   wherein the material configured to sense the gas is located within the etched recess portion of the dielectric membrane.

9. The gas sensing device according to claim 1, wherein the one or more polysilicon electrodes comprise a first polysilicon layer, and wherein the heater comprises a second polysilicon layer.

10. The gas sensing device according to claim 1, wherein the one or more polysilicon electrodes comprise a first polysilicon layer and a second polysilicon layer.

11. A gas sensor array assembly comprising:
an array of a plurality of gas sensing devices according to claim 1,
wherein the plurality of devices is formed on a single chip.

* * * * *